United States Patent [19]

Marcovici

[11] Patent Number: 5,796,153
[45] Date of Patent: Aug. 18, 1998

[54] VARIABLE-RESPONSE X-RAY DETECTION ASSEMBLIES AND METHODS OF USING SAME

[75] Inventor: Sorin Marcovici, Lexington, Mass.

[73] Assignee: Analogic Corporation, Peabody, Mass.

[21] Appl. No.: 527,268

[22] Filed: Sep. 12, 1995

Related U.S. Application Data

[63] Continuation-in-part of Ser. No. 436,572, May 8, 1995, Pat. No. 5,587,611.
[51] Int. Cl.[6] .................. H01L 31/105; H01L 31/117
[52] U.S. Cl. .................. 257/446; 257/458; 257/464; 257/428; 250/370.09; 250/370.11; 250/370.14
[58] Field of Search .................. 257/446, 458, 257/464, 428; 250/370.09, 370.11, 370.14

[56] References Cited

U.S. PATENT DOCUMENTS

| | | | |
|---|---|---|---|
| 4,282,541 | 8/1981 | Tsang | 257/458 |
| 4,914,301 | 4/1990 | Akai | 257/428 |
| 4,950,906 | 8/1990 | Beerlage | 250/370.09 |
| 5,151,588 | 9/1992 | Kiri | 250/370.09 |
| 5,360,987 | 11/1994 | Shibib | 257/461 |
| 5,465,002 | 11/1995 | Snoeys | 250/370.09 |

OTHER PUBLICATIONS

Promod Hague, "Scintillator crystal–photodiode array detectors" in Thomas H. Newton and D. Gordon Potts (eds.), *Technical Aspects of Computed Tomography*, vol. 5 at 4127–4132 (1981).

*Primary Examiner*—Jerome Jackson
*Attorney, Agent, or Firm*—Lappin & Kusmer

[57] ABSTRACT

Variable-response photodetectors adapted to compensate for nonuniformity along an axis of a scintillating crystal by means of multi-element photodiodes and systems for selectively activating different photodiode sub-elements are disclosed, together with arrays of such photodetectors and X-ray detection systems utilizing such photodetectors.

52 Claims, 3 Drawing Sheets

VARIABLE-RESPONSE X-RAY DETECTION ASSEMBLIES AND METHODS OF USING SAME

This application is a continuation-in-part of U.S. patent application Ser. No. 08/436,572 filed May 8, 1995, now U.S. Pat. No. 5,587,611, issued Dec. 24, 1996, and having a common assignee.

This invention relates generally to an improved X-ray detector assembly wherein a set of interconnectable photodiode sub-elements is associated with a single scintillating crystal, systems for regulating and integrating the response of the several photodiode sub-elements in relation to a particular detector assembly, and to multi-unit arrays of such detector assemblies for use in connection with X-ray detection apparatus.

BACKGROUND OF THE INVENTION

X-ray detection systems for such applications as computerized tomography commonly employ combinations of scintillating crystals and photodiodes. For example, a CAT scanner system operates by taking multiple, cross-sectional, X-ray slices from different angles within a single plane passing through a body. An X-ray source and an array of detectors are placed on opposite sides of an annular gantry, which rotates in the selected plane around the body. Signals generated by the detector array are digitized and mathematically processed to create a cross-sectional image of the body.

In a scintillating-photodiode X-ray detection system, the incident X-rays are absorbed by a scintillating crystal and converted into visible light. That visible light is then absorbed into a silicon photodiode, which converts the light into electron-hole pairs that diffuse from the P-N junction and thereby could generate a current flow. Because the current flow is typically of very small magnitude, it is common to use an amplification means to amplify the photodiode signal and convert it into a voltage. The output of such a scintillating-photodiode-preamplifier system is a voltage that is proportional in magnitude to the incident X-ray flux on the scintillating crystal. Systems of this type are described in a chapter by Promod Hague entitled "Scintillator crystal-photodiode array detectors" appearing in Thomas H. Newton and D. Gordon Potts (eds.), "Technical Aspects of Computed Tomography," vol. 5 at 4127–4132 (1981), which chapter is incorporated herein by reference.

In a typical X-ray detector construction, a thin, generally rectangular silicon wafer is appropriately doped so as to create a narrow P-type zone or region adjoining a first face of the wafer and a narrow N-type zone adjoining a second, opposite face, the P and N zones being separated by an almost intrinsic region in the interior portion of the wafer. For example, it is conventional to create P-type zones using a boron dopant and N-type zones using a phosphorus dopant. This photodiode is mounted on a substrate, for example, along the N-type face, and a correspondingly sized and shaped scintillating crystal is mounted along the P-type face using silicon grease or other optically-transparent epoxy as a coupling medium between the adjoining scintillating crystal and photodiode surfaces to form a single X-ray detector unit. Electrical terminals are connected respectively to the P and N zones to collect the current flow generated by the X-ray detector.

An important parameter in high-quality photodetector construction is the need to minimize the degree of detector nonuniformity, especially along the so-called "Z-axis," which, in the art, is defined as the axis parallel to the longer two sides of the typically rectangular photodetector unit. As conventionally prepared, X-ray scintillating crystals include various irregularities and nonuniformities which can affect the crystals' performance in converting impinging X-rays into light energy. Unless these crystal nonuniformities are corrected or compensated for, they could result in erroneous detector readings. Although crystal nonuniformities may occur throughout the crystal structure, their impact is particularly magnified along the relatively long Z-axis of the crystal. While nonuniformity along the relatively shorter X-axis of the crystal (which is an axis parallel to the short sides of the typically rectangular photodetector) may also affect crystal performance, these effects are generally less substantial and, therefore, less critical in a high-quality X-ray detector system.

In particular, crystal uniformity along the Z-axis has been found to be relatively high in the center portion of the crystal, while somewhat irregularly tapering off toward either end of the crystal. By making the crystal longer along the Z-axis than would otherwise be necessary, it is possible to expand that central, relatively high uniformity region thereby somewhat moderating the response nonuniformity over that portion of the crystal that is being used for detection. But this approach has both physical and cost limitations, and still could result in significant crystal response nonuniformity over a larger crystal region.

These and other problems with and limitations of X-ray detector design are largely overcome with the variable-response X-ray detectors and X-ray detector arrays for compensated detector assemblies in X-ray detection systems that combine the response of the several photodiode sub-elements of one or more X-ray detectors in accordance with this invention.

OBJECTS OF THE INVENTION

Accordingly, it is a general object of this invention to provide variable-response X-ray detectors which can compensate for scintillating crystal nonuniformities, as well as detector assemblies and X-ray detection systems and methods utilizing such variable-response X-ray detectors.

A principal object of this invention is to provide a multi-element X-ray detector assembly having a plurality of electrically-interconnectable photodiode sub-elements of variable size, location, and/or geometry.

A further object of this invention is to provide a X-ray detector assembly in which a scintillating crystal with Z-axis nonuniformity is matched to a semiconductor wafer having an interconnectable system of variably shaped and/or sized photodiode regions which are selectively activated to form a compensated X-ray detector unit.

Another object of this invention is to provide a system for modifying the Z-axis response of a X-ray detector unit by automatically and selectively activating or deactivating particular photodiode sub-elements of said unit in such a manner as to compensate for the particular scintillating crystal's Z-axis nonuniformity.

Still another object of this invention is to provide an array of variable-response X-ray detector units for X-ray detection.

Yet another object of this invention is to provide means for regulating, coordinating and integrating the overall Z-axis response of an array of variable-response X-ray detector units.

An overall object of this invention is to provide X-ray detection systems having improved performance and lower production costs than comparable prior art systems by utilizing variable-response photodiode units associated with each scintillating crystal element and arrays of such photodiode units having configurable Z-axis responses according to this invention.

These and other objectives and advantages of this invention will be better understood from the following description, which is to be read together with the accompanying drawings.

SUMMARY OF THE INVENTION

A variable-response X-ray detector assembly in accordance with this invention generally comprises an X-ray scintillating crystal having Z-axis nonuniformity and a specially-tailored set of electrically-interconnectable photodiode sub-elements, preferably of variable size or geometry, disposed along the Z-axis. For a particular scintillating crystal with a predetermined Z-axis response profile, the various photodiode sub-elements of the associated semiconductor wafer can be specially sized and located, and then be selectively activated or deactivated, to enhance more or less the signal over particular zones along the detector's Z-axis in such a manner as to compensate for the crystal's Z-axis nonuniformity. The precise ratio of the photodiode's sub-element regions and the corresponding compensatory effects on crystal nonuniformity of selectively activating one or more of those photodiode regions are specific to a given X-ray detector and adaptable for any crystal topology. These relationships can be computed and represented by an activation/deactivation algorithm which lends itself to computer-controlled implementation integrated with measuring scintillation crystals to automatically activate selected photodiode sub-elements to compensate for Z-axis crystal nonuniformity. Multiple variable-response X-ray detector units in accordance with this invention are utilized side-by-sin arrays as part of an overall X-ray detection system.

DETAILED DESCRIPTION OF THE INVENTION

In one conventional X-ray detector construction, a single scintillating crystal is paired with a single photodiode of similar dimensions. The single photodiode typically consists of a silicon wafer having a relatively wide band of a first doped region of a first polarity along a wafer surface, and separated by silicon bulk from a second doped region of opposite polarity. This conventional X-ray detector configuration, however, does not readily lend itself to correction or compensation for the almost unavoidable Z-axis nonuniformity of the crystal.

Figure 1:
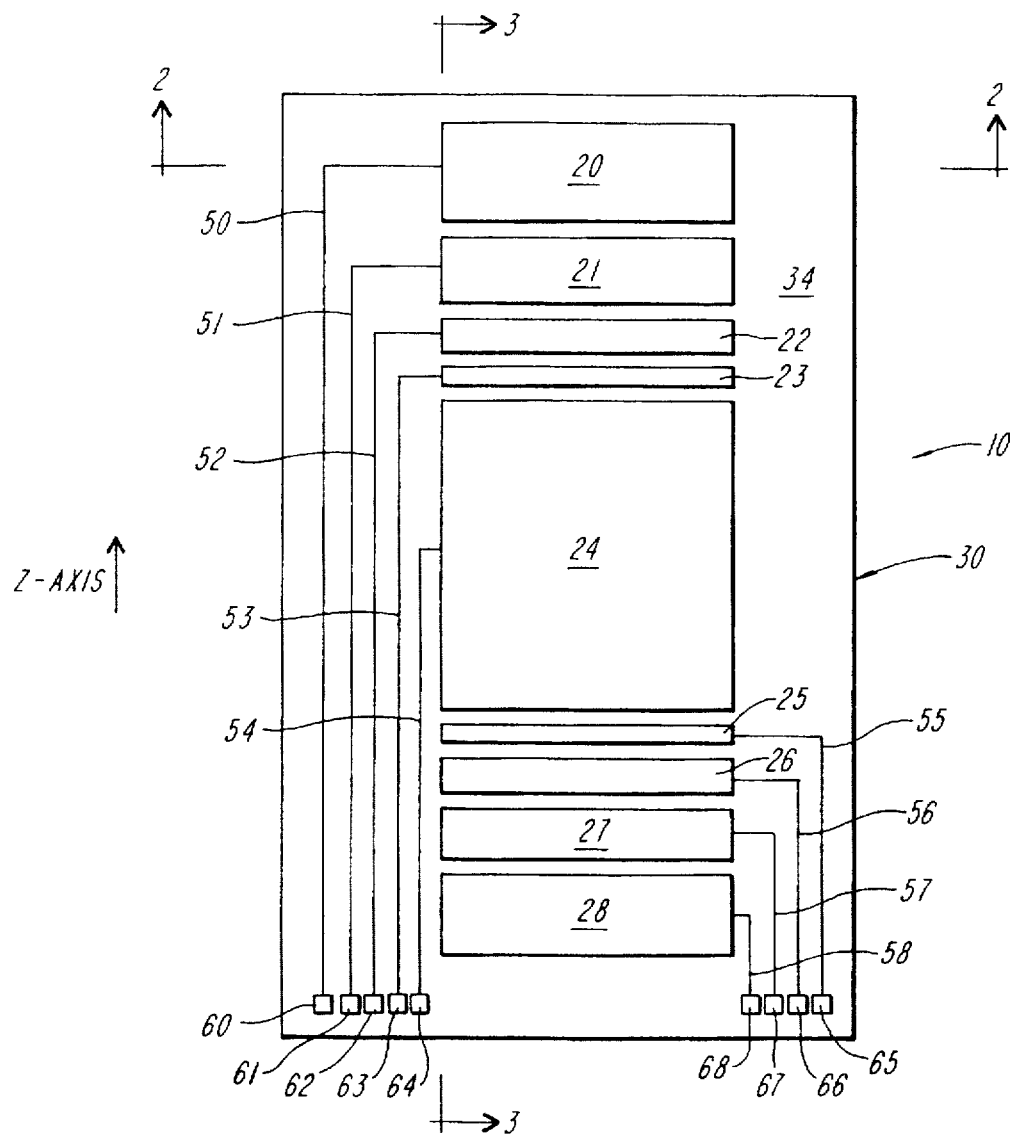
FIG. 1 is a top plan view of a set of interconnectible, variably-sized photodiode sub-elements according to this invention oriented along the Z-axis of the face of a semiconductor wafer.

In contrast with this conventional X-ray detector construction, FIG. 1 schematically illustrates a representative embodiment of the photodiode portion of a variable-response X-ray detector according to this invention. As shown in FIG. 1, the photodiode portion 10 of the variable-response X-ray detector comprises a set of photodiode regions, namely sub-elements 20, 21, 22, 23, 24, 25, 26, 27 and 28 disposed in generally parallel, rectangular configurations along the Z-axis of a single semiconductor wafer 30 made of silicon or other semiconductor material. Each photodiode sub-element 20-28 is associated respectively with an individual, metallized electrical connector 50-58 deposited on the surface 34 of wafer 30 and running from an end of its associated rectangular sub-element to an electrical terminal 60-68 respectively. Electrical terminals 60-68 are interconnectable through an electrical matrix (not shown) such that one or more of photodiode sub-elements 20-28 can be selectively simultaneously activated to compensate for Z-axis nonuniformity of the scintillating crystal, as described herein.

Figure 2:
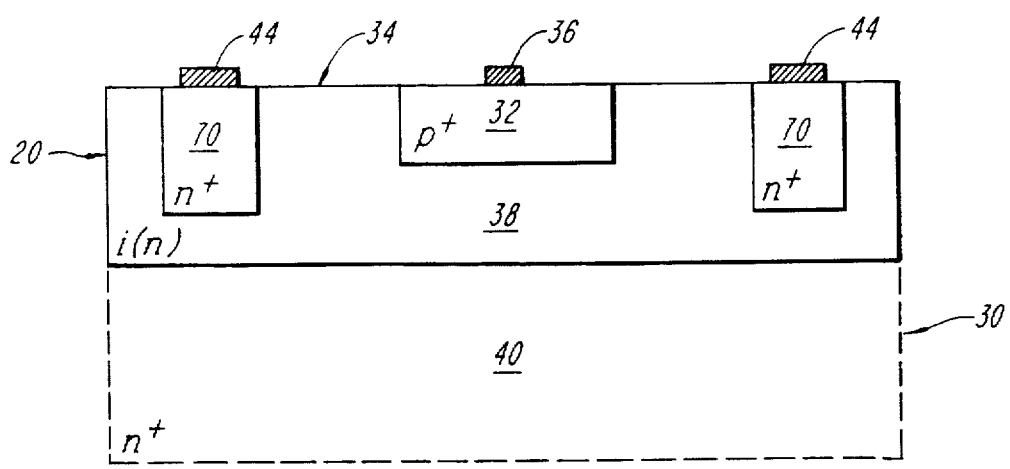
FIG. 2 is an enlarged schematic sectional view along the line 2—2 of FIG. 1.

As better seen in the sectional view of sub-element 20 in FIG. 2, each photodiode sub-element 20-28 preferably comprises a coplanar photodiode configuration as described in the commonly-assigned, U.S. patent application Ser. No. 08/436,572, now U.S. Pat. No. 5,587,611, of which this application is a continuation-in-part, and which application is incorporated herein by reference. Thus, in accordance with one embodiment of this invention, coplanar photodiode sub-element 20 comprises a portion of a silicon wafer 30 having a relatively shallow, centrally-located channel or band of P-doped (p+) region 32 flanked by somewhat deeper bands or channels of N-doped (n+) regions 70, formed along and adjacent planar surface 34 of the silicon wafer. P-doped region 32 and N-doped regions 70 are formed into a silicon bulk (i(n)) region 38. Alternating bands of region 32 and region 70 are also separated by bands of the silicon bulk region 38 as shown in FIG. 2. In a preferred embodiment of this invention, region 32 extends to a depth of about 1-2 microns from surface 34, whereas regions 70 extend to a depth of about 2-3 microns from surface 34. In another preferred embodiment of this invention, region 32 ranges from about 800-1000 microns in width, regions 70 range from about 200-750 microns in width, and the bands of region 38 separating adjacent bands of regions 32 and 70 range from about 10-25 microns in width.

Photodiode sub-element 20 illustrates a construction in which P-doped region 32 predominates along surface 34, as seen by the relatively greater width of region 32 as compared with N-doped regions 70. It will be understood that in an alternative and substantially equivalent embodiment of this invention, the predominant region 32 may be N-doped, and regions 70 would then be P-doped. It is necessary, however, that each photodiode sub-element 20-28 of a detector unit be similarly configured with respect to the respective P-doped and N-doped regions. In still another embodiment, silicon wafer 30 may further comprise another N-doped region 40 underlying region 38 so as to create a silicon bulk region 38 between N-doped region 40 and the alternating P and N-doped regions 32 and 70 along wafer surface 34. It will also be understood that in the above-described alternative construction of the coplanar photodiode sub-element, wherein the predominant region 32 is N-doped, underlying region 40 would be doped so as to have an opposite polarity (p+) from that of the predominant (n+) region along surface 34.

As discussed above, the predominant polarity region 32 (p+ as shown in FIG. 2) comprises a shallow band that is wider but typically shallower than the adjacent bands of opposite polarity 70 (n+ as shown in FIG. 2). Each predominant polarity region 32 is associated with a metallized electrical contact 36, and each opposite polarity region 70 is associated with a metallized electrical contact 44. Electrical contact 36 is connected at one edge of sub-element 20 to its associated electrical connector 50 (FIG. 1) going to terminal 60. It should be understood that the widths of electrical contacts 36 and 44 relative to bands 32 and 70 are illustrated out of proportion in FIG. 2 for purposes of illustration. Electrical contacts 36 and 44 should generally be kept as thin as possible to minimize any interference with or reflection of light passing between the scintillating crystal and photodiode sub-element 20.

Photodiode sub-element 20 as shown in FIG. 2 operates generally in similar fashion to conventional photodiodes, but with significantly improved results, as well as reduced manufacturing costs, owing to the optimized geometry of this construction. Thus, X-rays from an X-ray source enter the associated scintillating crystal, which converts the X-rays into blue light. The light photons from the scintillating crystal pass into the shallow P-doped region 32, penetrating only a few microns into the wafer, where they generate electron-hole pairs. The electrical charges thus generated diffuse respectively to the p+ and n+ regions of the sub-element, and from there to electrical contacts 36 and 44 respectively thereby generating an electrical current proportional to the flux of the X-rays absorbed into the scintillating crystal. In an arrangement of adjacent photodiode sub-elements, each constructed as shown in FIG. 2, bands 70 of opposite polarity flanking either side of predominant polarity band 32 to a depth as great as or somewhat greater than the depth of band 32, act as "channel stops" that minimize electrical crosstalk and reduce erroneous readings by blocking the spillover of electrical charges between adjacent photodiode sub-elements. The distance between adjacent bands 32 and 70 of either the same or an adjacent photodiode sub-element is kept small (on the order of about 10-25 microns) relative to the width of bands 32 and 70 so as to minimize the amount of light from a scintillating crystal that activates any part of the bulk silicon zone 38. Because the channel-stop bands 70 block electrical charge spillover to adjacent channels, any secondary charge generation will likely be collected by the proper band 32 or 70. It should be understood that in FIG. 2, the relative widths of the bands of bulk silicon 38 separating bands 32 and 70, as well as the depths of bands 32 and 70 relative to the overall thickness of the silicon wafer, have been exaggerated for illustrative purposes.

As shown in FIG. 1, photodiode portion 10 comprises nine distinct, rectangular photodiode sub-elements 20-28 formed along surface 34 in substantially parallel bands by selective doping of semiconductor wafer 30. In alternative embodiments of this invention, more or fewer photodiode sub-elements could be formed along surface 34, and those sub-elements could be formed in shapes other than rectangular bands, as appropriate for compensating for crystal response nonuniformity, subject only to physical and economic limitations. Thus, for example, a greater number of narrower sub-element bands across wafer surface 34 would permit more fine-tuning of the compensation for crystal nonuniformity.

At least in theory, for example, one or more of the photodiode sub-elements 20-28 could be further subdivided into a plurality of smaller rectangles or squares of doped region to create a two-dimensional array of independently activatable photodiode regions across surface 34, much like the rectangular array of pixels on a color video monitor. This configuration would make it possible to simultaneously compensate for X-axis as well as Z-axis crystal nonuniformity. However, given the current state of this technology and the related cost considerations, the use of nine bands of varying widths, as illustrated in FIG. 1, is considered the best mode at this time of practicing this invention.

Figure 3:
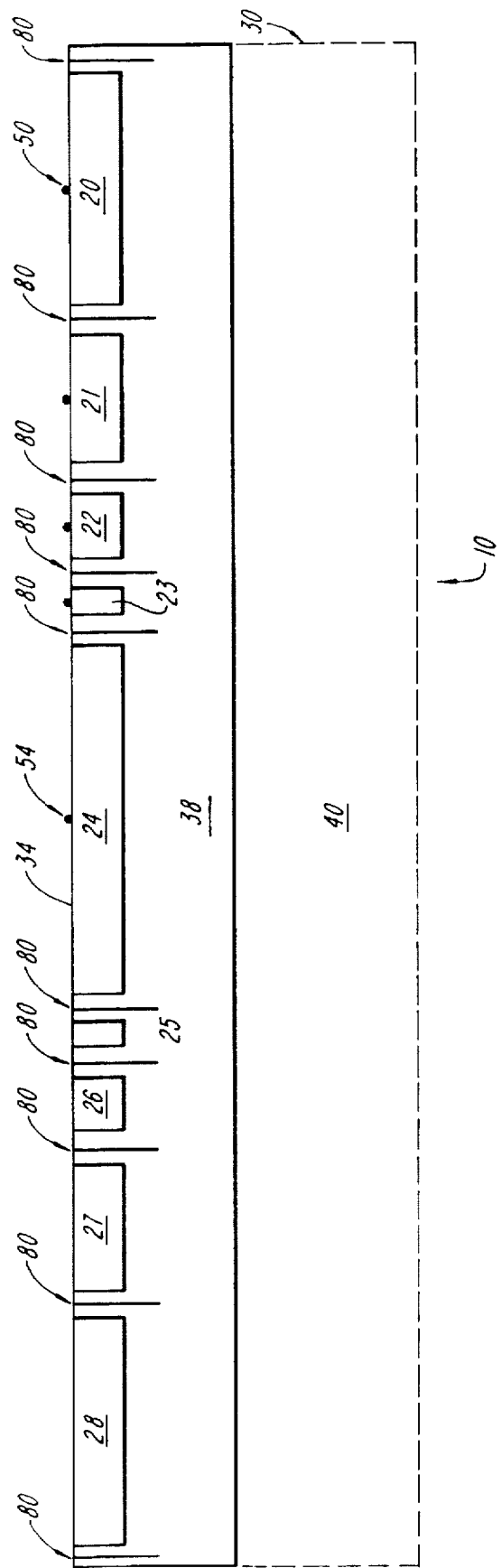
FIG. 3 is a schematic sectional view along the line 3—3 of FIG. 1.

As shown in FIG. 1, photodiode portion 10 comprises a set of photodiode sub-elements of generally rectangular area. As seen in FIG. 3, each sub-element is separated from each adjacent sub-element, as well as from the edges of wafer 30, by a relatively narrow band of bulk silicon 38 and by additional channel stops 80 positioned generally in the center of those separating bands of bulk silicon. The placement of a channel stop 80 at both edges of wafer 30 minimizes or eliminates electrical charge leakage associated with edge effects. Channel stops 80, comparable to channel stops 70 in FIG. 2, comprise regions of doped material having a polarity opposite from that of the predominant-doped regions, such as region 32 in FIG. 2. Channel stops 80 are generally narrower than channel stops 70, however, typically ranging from about 100-120 microns in width. Also similar to channel stops 70, channel stops 80 are seen to extend into wafer 30 to a depth at least as great as and, preferably, somewhat greater than the depths of the adjacent predominant-doped regions. The purpose of channel stops 80 is to electrically isolate each photodiode sub-element from adjacent sub-elements and to help prevent electrical charge generated in one sub-element from being collected by an adjacent sub-element and its associated electrical contact.

As previously discussed, the surface areas and/or shapes of sub-elements 20-28 along surface 34 may, in the broadest embodiments of this invention, be the same or different but, in a preferred embodiment as shown, sub-elements 20-28 have the same general rectangular shape but different surface areas. As shown, in FIG. 1, centrally-located, rectangular sub-element 24 has by far the largest surface area as measured along surface 34, and the relative surface areas of the peripheral sub-elements vary directly in relation to their respective distances from the center of surface 34. Thus, sub-elements 23 and 25, flanking sub-element 24 along the Z-axis, are of similar size and shape but have the smallest surface areas. Sub-elements 22 and 26, on either side respectively of sub-elements 23 and 25 along the Z-axis, are also of similar size and shape, both being of larger surface area than respective adjacent sub-elements 23 and 25. Similarly, sub-elements 21 and 27 are of similar size and shape but with larger surface areas than respective adjacent sub-elements 22 and 26. Finally, sub-elements 20 and 28, at opposite ends of wafer 30 along the Z-axis, are of similar size and shape, and, once again, have larger surface areas than respective adjacent sub-elements 21 and 27 but still smaller than central sub-element 24. This general type of sub-element configuration has been found effective in compensating for the most common type of crystal nonuniformity along the Z-axis when these sub-elements are selectively activated as described herein. But, it is also within the scope of this invention to utilize other sub-element configurations as appropriate for a particular crystal nonuniformity.

The variable-response X-ray detectors of this invention may be utilized in various ways to compensate for crystal nonuniformity. In one embodiment, a variable-response photodiode as shown in FIG. 1, more or less adaptable to a typical crystal topology, is mated to an X-ray scintillating crystal such that their respective Z-axes are in alignment. Crystal response nonuniformity along the Z-axis is then determined by conventional techniques, and one or more of the photodiode sub-elements is selectively simultaneously activated through the interconnected electrical matrix to achieve optimum compensation of the crystal's Z-axis nonuniformity.

In another, more sophisticated embodiment, a variable-response photodiode in accordance with this invention can be custom-tailored to the nonuniform response profile of a particular crystal. Selective activation (connection) or deactivation (disconnection) of various photodiode sub-elements can then be used to fine-tune the detector unit's responsiveness. In still another embodiment, the relationship of a photodiode's various sub-element areas to the topology of a given crystal can be expressed mathematically as an algorithm, and that algorithm can be utilized in computer-controlled instrumentation for controlling automatically the interconnecting of various photodiode sub-elements in order to optimize the compensation of crystal nonuniformity.

The embodiments of the present invention described are intended to be taken in an illustrative and not a limiting sense. Various modifications and changes may be made to these embodiments by persons skilled in the art without departing from the scope of the present invention as defined in the appended claims.

I claim:

1. A coplanar, non-dielectrically isolated photodiode for X-ray detection comprising semiconductor means having an absorption face and adjoining said face: (a) a first doped region having a first polarity and defined by planar walls extending substantially perpendicularly from said absorption face into said semiconductor means to a first depth; (b) a second doped region having a polarity opposite that of said first doped region and defined by planar walls extending substantially perpendicularly from said absorption face into said semiconductor means to a second depth that is substantially equal to or greater than said first depth; (c) at least a third doped region having the same polarity as that of said first doped region and defined by planar walls extending substantially perpendicularly from said absorption face into said semiconductor means to a third depth, said second doped region being spaced from said first doped region along a first axis, and said third doped region being spaced from said first doped region along a second axis which is orthogonal to said first axis; (d) a substantially undoped region extending from said absorption face into said semiconductor means so as to separate and completely surround said first, second and third doped regions and to create a single p-n junction between said first and second doped regions; and (e) first-polarity electrical contact means connected to said first and third doped regions along said absorption face for selectively activating said first and third doped regions individually or simultaneously.

2. A photodiode according to claim 1 wherein said electrical contact means comprises first-polarity electrical contact means connected respectively to said first and third regions along said absorption face.

3. A photodiode according to claim 2 further comprising an electrical matrix interconnecting each of said first-polarity electrical contact means.

4. A photodiode according to claim 2 further comprising a fourth doped region having a polarity opposite that of said first doped region, said fourth doped region being located between said first and third doped regions and being defined by planar walls extending substantially perpendicularly from said absorption face into said semiconductor means to a fourth depth which is greater than said first or third depths, said fourth doped region also being completely surrounded by said substantially undoped region.

5. A photodiode according to claim 4 further comprising opposite-polarity electrical contact means connected to said fourth doped region along said absorption face.

6. A photodiode according to claim 1 comprising at least two adjacent photodiode sub-regions on the same semiconductor means, each of said sub-regions comprising a combination of said first, second and at least a third doped regions and said substantially undoped region, said adjacent sub-regions being spaced from one another along said second axis and separated by said substantially undoped region.

7. A photodiode according to claim 6 wherein said first-polarity electrical contact means can selectively activate any one or more of said first and third doped regions.

8. A photodiode according to claim 6 further comprising a fourth doped region having a polarity opposite that of said first doped region, said fourth doped region being located between adjacent sub-regions and being defined by planar walls extending substantially perpendicularly from said absorption face into said semiconductor means to fourth depth which is greater than said first or third depths, said fourth doped region also being completely surrounded by said substantially undoped region.

9. A photodiode according to claim 7 wherein only some of said first and third doped regions are activated at a particular time.

10. A photodiode according to claim 6 wherein said first and third doped regions comprise alternating, substantially parallel first-polarity bands disposed along said second axis along said absorption face, said first-polarity bands being separated by alternating, substantially parallel opposite-polarity bands.

11. A photodiode according to claim 10 wherein at least some of said first-polarity bands are of different widths.

12. A photodiode according to claim 11 wherein the widest first-polarity band is located substantially centrally along said second axis along said absorption face.

13. A photodiode according to claim 12 wherein the narrowest of said first-polarity bands are adjacent each side of said widest first-polarity band.

14. A photodiode according to claim 13 wherein additional first-polarity bands beyond said narrowest first-polarity bands become increasingly wider as they approach the opposite edges of said absorption face.

15. A photodiode according to claim 14 comprising a total of nine said first-polarity bands and nine separate electrical contact means connected respectively to said nine bands along said absorption face.

16. A photodiode according to claim 10 wherein said absorption face is substantially rectangular and said first-polarity bands are oriented substantially at right angles to the longitudinal axis of said face.

17. A photodiode according to claim 1 wherein the total surface area of first-polarity regions along said absorption face is greater than the total surface area of opposite-polarity regions along said absorption face.

18. A photodiode according to claim 1 wherein said first and third depths range from about 1–2 microns.

19. A photodiode according to claim 4 wherein said fourth depth ranges from about 2–3 microns.

20. A photodiode according to claim 8 wherein each of the first-polarity regions extend into said semiconductor means to a depth of about 1–2 microns and each of the opposite-polarity regions extend into said semiconductor means to a depth of about 2–3 microns.

21. A photodiode according to claim 6 wherein said electrical contact means comprises a separate first-polarity electrical contact connected respectively to each of the first-polarity regions along said absorption face.

22. A photodiode according to claim 21 further comprising an electrical matrix interconnecting each of said first-polarity electrical contacts.

23. A photodiode according to claim 21 further comprising an opposite-polarity electrical contact connected respectively to each of the opposite-polarity regions along said absorption face.

24. A photodiode according to claim 1 wherein said semiconductor means comprises a silicon wafer.

25. A photodiode according to claim 6 wherein said semiconductor means comprises a silicon wafer.

26. Apparatus for detecting the light produced by X-rays absorbed in a scintillating crystal, said apparatus comprising non-dielectrically isolated, multi-region photodiode means comprising at least two pairs of P-doped and N-doped regions, each said pair comprising a single p-n junction, wherein said doped regions extend from a single planar surface of said photodiode means into said photodiode means and associated electrical contacts for each P-doped region, each N-doped region, or both, said electrical contacts being positioned along said single planar surface, further wherein said P-doped and N-doped regions are separated by a substantially undoped region extending from said planar surface into said photodiode means so as to completely surround each said P-doped and N-doped region; further wherein adjacent pairs of P-doped and N-doped regions are separated by said substantially undoped region and a doped separation layer.

27. Apparatus according to claim 26 wherein either said P-doped or N-doped regions predominate along said planar surface, so as to establish predominant and non-dominant doped regions as determined by comprising the respective surface areas of P-doped and N-doped regions along said planar surface, and an electrical matrix interconnects the electrical contacts associated with each of the predominant-doped regions.

28. Apparatus according to claim 27 wherein each non-dominant doped region extends into said photodiode means to a depth substantially equal to or greater than the depth of adjacent predominant-doped regions.

29. Apparatus according to claim 28 wherein at least two of said predominant-doped regions are of different surface areas as measured along said planar surface.

30. Apparatus according to claim 29 wherein the predominant-doped region most centrally located on said planar surface has a larger surface area than any of the peripheral predominant-doped regions.

31. Apparatus according to claim 30 further wherein the surface areas of peripheral predominant-doped regions become larger as their respective distances from a centerline of said planar surface become greater.

32. Apparatus according to claim 28 wherein said predominant-doped regions comprise a relatively wide band of the doped material running along a centerline of said planar surface and, on either side thereof, a set of four narrower bands of the doped material.

33. Apparatus according to claim 28 further comprising a polarity of said multi-region photodiode structures aligned in side-by-side relationship.

34. Apparatus according to claim 29 further comprising a scintillating crystal fixed to said semiconductor planar surface to form a variable-response detector unit, said crystal having response nonuniformity along at least one axis thereof, and further wherein said predominant-doped regions of different surface areas are disposed along said planar surface so as to compensate for said crystal response nonuniformity when one or more of the predominant-doped regions are selectively activated.

35. Apparatus according to claim 34 further comprising a plurality of said variable-response detector units aligned in side-by-side relationship.

36. Apparatus according to claim 34 further comprising means for determining the crystal's response nonuniformity and for automatically selectively activating said predominant-doped regions to compensate therefor.

37. Apparatus according to claim 34 wherein only some of said predominant-doped regions are activated at a particular time.

38. In an X-ray detection system comprising in combination an X-ray source; scintillating crystal means to convert X-ray radiation into light, said crystal means having response nonuniformity along at least one axis thereof; non-dielectrically isolated photodiode means to convert light into electrical current, said crystal means and photodiode means being mutually glued along an interface therebetween to form a detector unit; frame means for positioning the crystal and photodiode means relative to said X-ray source; electrical conductor means for collecting electrical charges generated in the photodiode means; and electrical means for converting the electrical signals from the photodiode means into measurements of X-ray detection; the improvements comprising: adjacent said interface, at least two pairs of P-doped and N-doped regions for each of said photodiode means, each said pair comprising a single p-n junction, wherein each of said P- and N-doped regions is separated from one another and from adjacent P-N pairs by bands of undoped material, the less-dominant of each said doped region of a pair surrounding at least a portion of the perimeter of the associated predominant-doped region and extending into the photodiode means to a depth substantially equal to or greater than the depth of said predominant-doped region, electrical contacts associated respectively with at least each of the predominant-doped regions and located along said interface, and an electrical matrix interconnecting all of the electrical contacts associated with the predominant-doped regions.

39. The X-ray detection system of claim 38 further wherein a plurality of said detector units are aligned in an array in side-by-side relationship.

40. The X-ray detection system of claim 39 further wherein each said detector unit comprises at least two of said predominant-doped regions which are of different surface areas as measured along said interface.

41. The X-ray detection system of claim 40 further wherein the predominant-doped region most centrally located on said interface of each detector unit comprises a generally rectangular band with a larger surface area than any of the peripheral predominant-doped regions.

42. The X-ray detection system of claim 41 further wherein each said centrally-located predominant-doped region is flanked on either side thereof by a set of narrower, generally rectangular bands of predominant-doped region.

43. The X-ray detection system of claim 42 further wherein said interface is generally rectangular and said bands run across said interface.

44. The X-ray detection system of claim 38 wherein said photodiode means comprises a doped silicon wafer.

45. The X-ray detection system of claim 44 further wherein said predominant-doped regions extend into said silicon wafer to a depth of about 1–2 microns and said less-dominant doped regions extend into said silicon wafer to a depth of about 2–3 microns.

46. A method of compensating for crystal response nonuniformity in an X-ray detector unit comprising a scintillating crystal glued with an optical epoxy to a planar surface of a photodiode, said method comprising the following steps: (a) doping silicon so as to create a photodiode having an absorption face and, adjacent said absorption face, at least two pairs of P-doped and N-doped regions, each said pair comprising a single p-n junction, wherein each of said P- and N-doped regions is separated from one another and from adjacent P-N pairs by bands of undoped material, the less-dominant of each said doped region of a pair surrounding at least a portion of the perimeter of the associated predominant-doped region and extending into the photodiode means to a depth substantially equal to or greater than the depth of said predominant-doped region, electrical contacts associated respectively with at least each of the predominant-doped regions and located along said absorption face; (b) electrically interconnecting each of said predominant-doped regions; (c) affixing a correspondingly sized X-ray scintillating crystal to said photodiode surface in alignment therewith; (d) determining crystal nonuniformity by measuring the uncompensated response of said crystal along at least one axis thereof; and (e) selectively simultaneously activating one or more of said electrically-interconnected predominantly-doped regions so as to compensate for said crystal nonuniformity.

47. A method according to claim 46 wherein said crystal nonuniformity along at least one crystal-axis is pre-determined and the size and location of said predominant-doped regions of said photodiode are pre-selected so as to compensate for said crystal nonuniformity.

48. A method according to claim 46 wherein said predominant-doped regions comprise a series of generally rectangular bands aligned along an axis which corresponds to the crystal axis having the greatest response nonuniformity.

49. A method according to claim 46 further comprising the steps of determining said crystal's response profile along at least one axis thereof, representing said response profile mathematically on computer software, and automatically implementing compensation of said response nonuniformity through computerized activation of one or more of said predominantly-doped regions.

50. A method according to claim 49 further comprising the step of adjusting the level of compensation by said computerized activation to obtain a pre-determined detector response output.

51. A coplanar, non-dielectrically isolated photodiode for X-ray detection comprising semiconductor means having an absorption face and, adjoining said face, a plurality of photoresponsive sub-regions, each of said sub-regions comprising: (a) a single, elongated first doped region having a first polarity and defined by planar walls extending substantially perpendicularly from said absorption face into said semiconductor means to a first depth; (b) a second doped region having a polarity opposite that of said first doped region and defined by planar walls extending substantially perpendicularly from said absorption face into said semiconductor means to a second depth that is substantially equal to or greater than said first depth; (c) a substantially undoped region extending from said absorption face into said semiconductor means so as to separate and completely surround both of said first and second regions and to create a single p-n junction between said first and second doped regions; and (d) first electrical contact means connected to said first region along said absorption face; wherein said sub-regions are disposed in substantially parallel bands along said absorption face and adjacent sub-regions are separated from one another by said substantially undoped region.

52. A photodiode according to claim 51 further wherein adjacent sub-regions are also separated by a separation layer of semiconductor doped to have a polarity opposite that of said first doped region, said separation layer being defined by planar walls extending substantially perpendicularly from said absorption face into said semiconductor means to a depth greater than said first depth.

* * * * *